(12) United States Patent
Li

(10) Patent No.: US 7,653,496 B2
(45) Date of Patent: Jan. 26, 2010

(54) FEATURE SELECTION IN MASS SPECTRAL DATA

(75) Inventor: Xiangdong Don Li, Union City, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 545 days.

(21) Appl. No.: 11/670,955

(22) Filed: Feb. 2, 2007

(65) Prior Publication Data

US 2007/0176088 A1 Aug. 2, 2007

Related U.S. Application Data

(60) Provisional application No. 60/764,729, filed on Feb. 2, 2006.

(51) Int. Cl.
*G06F 3/00* (2006.01)

(52) U.S. Cl. .................. 702/30; 702/2; 702/22
(58) Field of Classification Search ............ 702/2, 702/5, 19, 20, 22, 23, 30; 435/4, 6
See application file for complete search history.

(56) References Cited

U.S. PATENT DOCUMENTS 5,699,269 A * 12/1997 Ashe et al. ............... 702/30
7,499,807 B1 * 3/2009 Tolmachev et al. ........ 702/23

* cited by examiner

*Primary Examiner*—Kiet T Nguyen

(57) ABSTRACT

The present invention provides, inter alia, methods of analyzing mass spectral data. In some embodiments, the methods can be used for differential profiling of samples, such as comparing a sample comprising a compound and a sample comprising metabolites of the same compound. The methods can also be used to identify and isolate biomarkers. Systems for performing the methods, as well as computer-readable media for performing the methods, are also described.

20 Claims, 6 Drawing Sheets

FEATURE SELECTION IN MASS SPECTRAL DATA

RELATED APPLICATION

This application claims the benefit of U.S. Provisional Patent Application No. 60/764,729, filed Feb. 2, 2006, which is herein incorporated by reference in its entirety.

BACKGROUND

Recent advances in biotechnology, such as the sequencing of the human genome, have increased the need for information on how various encoded gene products, or proteins, mediate the biological processes that either contribute to health, or cause diseases. Standard molecular biological techniques study these processes at the genomic level, but do not provide information at the protein level. The growing field of proteomics research involves the search for targets or biomarkers for drug discovery and development, as well as to provide information that can be used to diagnose disease.

Comprehensive system-wide biomarker discovery has been made easier by the advent of large-scale analytical methods such as DNA microarray technology, high-throughput mass spectrometry (MS) and other techniques used to study complex biological systems. Statistical and machine-learning methods have also been developed, allowing the study of very large datasets produced by high-throughput protein analysis methods.

High throughput MS is a powerful technique in biomarker discovery. However, the use of this technique is complicated by a number of factors. Biological samples are very complex, and often contain hundreds to thousands of compounds, and analysis of these samples can often be difficult. For example, the differential comparison of LC-MS data from different biological samples generates complex datasets, and presents significant data processing challenges. The analysis is time-consuming and there is often significant noise and variability that is not properly accounted for. Current methods to eliminate noise and detect mass spectral peaks use an ad hoc approach, and do not use any a priori or learned information with regard to peak shape, retention time, or relationship among peaks. Statistical methods used to subtract background and reduce noise often remove relevant information in addition to filtering out noise and irrelevant information. The resulting data sets are not suitable for downstream analysis during biomarker discovery.

Therefore, there is a need for methods to analyze complex MS data sets that will incorporate richer qualitative information and thereby improve biomarker analysis. One way to address these challenges is by using a software module that contains a means for a priori partitioning of features, such that irrelevant features are filtered out before performing differential analysis of the data, while preserving relevant features for later analysis. If molecular features corresponding to specific chemical properties can be extracted in a fast and efficient manner, the data obtained can be used to make a powerful bioinformatics system.

DESCRIPTION OF THE INVENTION

Figure 1:
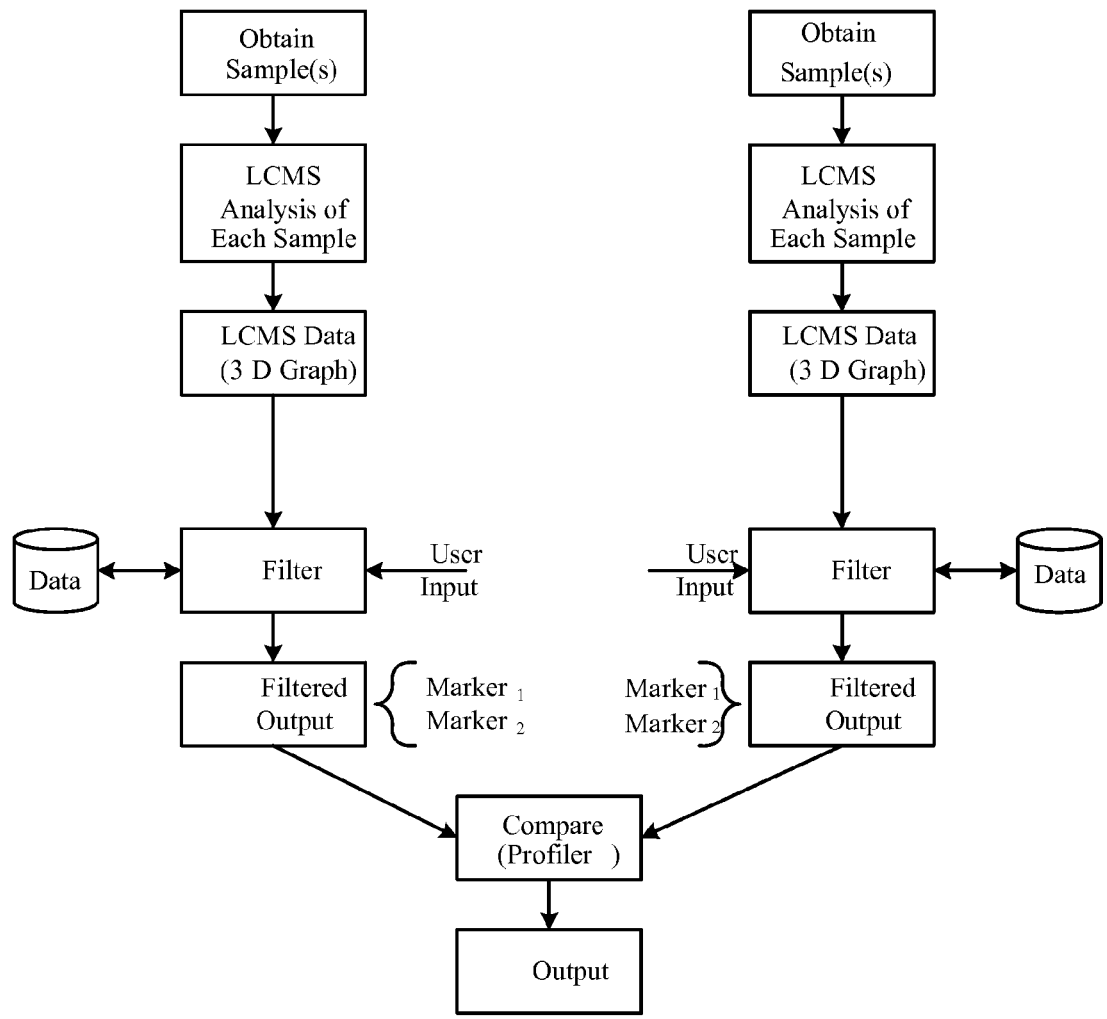
FIG. 1 is a diagram representing a method for the differential analysis of two complex biological samples using one method of this invention.

The present invention relates to, inter alia, methods for differential profiling of samples. In particular, some embodiments of the methods of the present invention integrate chemical information with differential expression analysis and statistical methods to identify or differentiate expression level changes in a biological sample.

In some embodiments, the methods of the present invention use a molecular feature extraction process to group mass peaks in mass spectrometric data sets. In an aspect, the peaks are grouped according to particular chemical features or properties. Extracted molecular feature information is then normalized and statistically or visually analyzed to identify differentially expressed features.

In some embodiments, the methods of the present invention combine chemical information with differential expression analysis, thereby significantly reducing noise. In an aspect, using chemically relevant information to extract molecular features also reduces the complexity of the input data for the differential expression analysis.

The present invention provides improved methods for rapid and accurate identification of differentially expressed entities in biological samples. Therefore, the methods of the present invention can be used to compare complex sets of data for various samples, and is particularly useful in biomarker discovery.

Various embodiments of the present invention will be described in detail with reference to the drawings, wherein like reference numerals represent like parts throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Prior to describing the invention in further detail, the terms used in this application are defined as follows unless otherwise indicated.

DEFINITIONS

Unless defined otherwise, all technical and scientific terms used herein have the same meaning as commonly understood to one of ordinary skill in the art to which this invention belongs. Although any methods, devices and material similar or equivalent to those described herein can be used in the practice or testing of the invention, the preferred methods, devices and materials are now described.

All publications cited in this specification, including patent publications, are indicative of the level of ordinary skill in the art to which this invention pertains and are incorporated herein by reference in their entireties.

As used herein, the term "differential profiling" or "differential display" refers to investigating the differences between the mass spectral data for a first sample and those for a second sample. Similarly, differential profiling can be performed for more than two sets of data, namely comparing the mass spectral data of three or more samples and investigating the differences among them. It should be noted that sometimes differential profiling is performed using sample sets, each of which comprises multiple samples. For instance, a user may wish to compare the molecules in the sera of breast cancer patients and those in the sera of normal controls. Thus, serum samples from multiple breast cancer patients are obtained, and serum samples from multiple normal controls are also collected. Each sample is analyzed, and differential profiling is conducted to compare the mass spectral data of the samples in the patient group to the mass spectral data of the control group. A differential display image or plot shows the differences between or among the samples, with respect to abundance of a particular component, presence of a particular chemical species, or changes in expression level of a particular component.

The term "sample" as used herein relates to a material or complex mixture of materials, typically, although not necessarily, in fluid form. Samples of the present invention include, but are not limited to, biological samples obtained from natural biological sources, such as cells or tissues, or plants. The samples of the present invention include, but are not limited to, complex biological samples containing many different components or metabolites, such as urine or serum, for example. The samples of the present invention also include complex mixtures derived from non-animal sources, such as complex extracts derived from plants. The sample may also be non-biological, such as environmental samples (water, air, rain, etc.)

The term "spectral peak" refers to a peak in the output from any type of spectral analysis instrument, and is known in the art. In a given analysis, peaks can represent one or more components in a sample. A "mass spectral peak" is a spectral peak in a mass spectrum.

The term "3-D peak" refers to a cluster of LC-MS (or GC-MS, CE-MS, etc.) signals that have the same m/z value (subject to variations in measurement), and similar retention time values. The signals could be either raw profile spectral pixels or spectral peaks.

In this specification and the appended claims, the singular form "a," "an," and "the" include plural reference unless the context clearly dictates otherwise. Unless defined otherwise, all technical and scientific terms used herein have the same meaning as commonly understood to one of ordinary skill in the art to which this invention belongs.

Methods for Analysis of Samples

To reduce the complexity of the mass spectral data obtained from a sample, the spectral peaks that are related to the same compound are grouped together. This can be achieved by analyzing the features of the various spectral peaks. Specifically, spectral peaks of similar retention time (RT) and mass to charge ratio (m/z) are grouped, optionally also taking into consideration other properties such as isotope clustering, mass, adduct formation, dimer formation, and/or trimer formation. An exemplary grouping is demonstrated in Table 1 below, which shows eight feature groups that elute at approximately the same time in a liquid chromatography column.

TABLE 1

Exemplary Feature Groups

| Group | species | RT | m/z | mass | abundance |
|---|---|---|---|---|---|
| 1 | M | 2.037 | | 310.0743 | 4195152 |
| | M + H | 2.037 | 311.0819 | 310.0746 | 2293700 |
| | M + H + 1 | 2.037 | 312.0838 | | 281053 |
| | M + H + 2 | 2.037 | 313.0796 | | 89762 |
| | M + H + 3 | 2.036 | 314.0822 | | 9620 |
| | M + H + 4 | 2.034 | 315.0858 | | 1271 |
| | M + Na | 2.038 | 333.0629 | 310.0737 | 681860 |
| | M + Na + 1 | 2.038 | 334.0652 | | 76900 |
| | M + Na + 2 | 2.038 | 335.0619 | | 25150 |
| | M + Na + 3 | 2.04 | 336.0628 | | 3048 |
| | 2M + Na | 2.036 | 643.1359 | 310.0734 | 267980 |
| | 2M + Na + 1 | 2.036 | 644.1388 | | 65029 |
| | 2M + Na + 2 | 2.036 | 645.1358 | | 26983 |
| | 2M + Na + 3 | 2.036 | 646.1369 | | 5102 |
| | 2M + Na + 4 | 2.033 | 647.1357 | | 1155 |
| | 2M + Na + 5 | 2.045 | 648.1414 | | 145 |
| 2 | M | 2.036 | | 310.3532 | 86544 |
| | M + H | 2.036 | 311.3602 | 310.3529 | 79826 |
| | M + H + 1 | 2.035 | 312.356 | | 881 |
| | M + Na | 2.036 | 333.3464 | 310.3572 | 5838 |
| 3 | M | 2.037 | | 369.1474 | 59441 |
| | M + H | 2.037 | 370.1547 | 369.1474 | 48982 |
| | M + H + 1 | 2.037 | 371.1566 | | 8742 |
| | M + H + 2 | 2.036 | 372.1538 | | 1717 |
| 4 | M | 2.037 | | 355.1317 | 40265 |
| | M + H | 2.037 | 356.1389 | 355.1317 | 34295 |
| | M + H + 1 | 2.038 | 357.1418 | | 5969 |
| 5 | M | 2.038 | | 468.0295 | 13908 |
| | M + H | 2.038 | 469.0368 | 468.0295 | 8874 |
| | M + H + 1 | 2.04 | 470.0376 | | 1442 |
| | M + H + 2 | 2.038 | 471.0452 | | 403 |
| | M + Na | 2.037 | 491.0186 | 468.0294 | 2004 |
| | M + Na + 1 | 2.036 | 492.0178 | | 166 |
| | 2M + H | 2.033 | 937.0685 | 468.0306 | 260 |
| | 2M + H + 1 | 2.041 | 938.061 | | 74 |
| | 2M + Na | 2.035 | 959.0463 | 468.0285 | 176 |
| 6 | M | 2.036 | | 778.1027 | 9792 |
| | M + H | 2.036 | 779.1102 | 778.1029 | 6379 |
| | M + H + 1 | 2.036 | 780.1115 | | 1863 |
| | M + H + 2 | 2.039 | 781.1053 | | 914 |
| | M + H + 3 | 2.032 | 782.1132 | | 167 |
| | M + Na | 2.031 | 801.088 | 778.0988 | 382 |
| | M + Na + 1 | 2.036 | 802.0854 | | 87 |
| 7 | M | 2.037 | | 664.1093 | 8630 |
| | M + H | 2.037 | 665.1164 | 664.1091 | 5531 |
| | M + H + 1 | 2.037 | 666.1182 | | 1478 |
| | M + Na | 2.036 | 687.0991 | 664.1099 | 1196 |
| | M + Na + 1 | 2.032 | 688.1061 | | 424 |
| 8 | M | 2.039 | | 354.0369 | 6416 |
| | M + H | 2.039 | 355.0442 | 354.0369 | 6010 |
| | M + H + 1 | 2.033 | 356.0482 | | 407 |

Thus, the first broad group in Table 1 relates to a compound (M) and comprises three subgroups. The first subgroup comprises M associated with a hydrogen (M+H), and four other species that are also M+H but differ in isotope compositions (M+H+1, M+H+2, M+H+3, M+H+4). Isotope clustering is explained in more detail in Example 1 of the present application. The second subgroup comprises the sodium adducts of M (M+Na), including species with different isotope compositions. The third subgroup comprises dimers of M (2M) with sodium, again including species with different isotope compositions. The other seven groups are similarly listed. The compound (also called molecular feature) that each group relates to is designated M and shown in bold with its average RT, mass, and cumulative abundance.

These eight groups in Table 1 formed one peak in liquid chromatography and many peaks in subsequent mass spectrometry in various places. Upon grouping as shown above, however, their relationship becomes clear, which not only facilitates differential profiling, but also enables a practitioner to compare the properties of each compound to the spectral behavior of known compounds in an effort to identify the compounds in the sample.

Thus, some embodiments of the present invention provide a method for analyzing mass spectral data of a sample, comprising dividing the mass spectral data into feature groups, each feature group relating to a compound, wherein said dividing is performed based on retention time, mass to charge ratio, and optionally at least one property selected from the group consisting of isotope clustering, mass, adduct formation, dimer formation, and trimer formation. The method may further comprise comparing the properties of any feature group to those of known compound in order to identify the compound(s) in the feature group.

The present invention further provides methods for differential profiling of multiple samples, by extracting chemically relevant information, followed by differential expression analysis. Chemically relevant information is extracted using a computerized algorithm that automatically extracts unique features from a data set. The extracted features are then differentially analyzed using a combination of statistical and visual methods. Thus, each one mass spectral data set obtained from a sample can be analyzed by the feature grouping process described above. The grouped data derived from multiple samples are then compared to each other or one another to identify compounds that are present in one or some, but not all, of the samples, or compounds of which the abundance changes significantly between or among the samples. The results can be used, for example, to identify compounds that increase or decrease in a diseased sample versus the normal control; an animal that has been fed with a carcinogen versus the normal control; a water sample from a potentially polluted area versus an unpolluted area; and the like.

To further facilitate the mass spectral analysis, and particularly the differential profiling, the data can be filtered by criteria determined by the user. As described in Example 1, the user can choose a specific range of retention time and/or mass to include in the analysis. Similarly, the user can choose the isotope pattern, charge state, abundance, etc. of the spectral peaks that the user wishes to include in the analysis. For example, if the user only wants to look for peptide markers that change in abundancy between or among the samples being analyzed, the peptide filter can be selected (see Example 1 and FIG. 3). If the user only wants small molecules to be analyzed or displayed, a mass range can be prescribed.

A simplified representation of certain embodiments of the method is shown in FIG. 1. In these embodiments, a biological sample containing a complex mixture of chemical components is obtained and then analyzed by any of one or more spectral analysis methods, such as LC-MS, for example. Spectral peaks obtained from the LC-MS analysis are grouped according to m/z ratio and retention time into 3-D peaks. The peak volume can be measured for ach 3-D peak. The molecular features are extracted as clusters of these 3-D peaks, using an algorithm that filters out irrelevant features while associating or grouping 3-D peaks according to chemically relevant information. For example, 3-D peaks can be associated as isotope clusters, dimers, adducts, etc. Peaks can be grouped according to chemical information available from a database, or based on user input. The extracted molecular features are listed in the output and can be used to identify different chemical components (or markers). The samples are then differentially profiled by comparing the extracted features (i.e. the filtered output) with the filtered output for a second biological sample, or by comparing the filtered output with molecular features extracted from known compounds.

In some embodiments, the present disclosure describes a method for differential profiling of highly complex biological samples. Samples of the present invention include, but are not limited to, biological samples obtained from natural biological sources, such as cells or tissues. In an aspect, the sample is a highly complex mixture of different components. The components may include, but are not limited to, proteins, metabolites, amino acids, glycerol esters, fatty acids, etc., and any derivatives or degradation products thereof. In an aspect, the sample contains hundreds to thousands of components, spanning a broad range of compositions and concentrations. In yet another aspect, the sample is a complex mixture of peptides or nucleic acids. In some embodiments, the sample is a complex mixture of metabolites present in a biological sample. In some embodiments, the sample is a complex mixture of small molecules.

The present disclosure describes methods for analyzing a complex mixture of various components. In some embodiments, the analysis begins with separating portions of the sample into multiple components. The sample can be separated using any of a number of separation techniques including, but not limited to, ion exclusion, ion exchange, normal/reversed phase partition, size exclusion, ligand exchange, liquid/gel phase isoelectric focusing, adsorption chromatography, and liquid chromatography. In an aspect, the components are separated by liquid chromatography (i.e. LC, such as HPLC). Each separated component is associated with a specific retention time. Variation in retention time can be reduced using flow-controlled capillary HPLC. The separated components are then further analyzed by mass spectrometry (MS) methods, to determine the identity of the separated components.

The MS analysis can be performed by using any MS method or instrumentation. In some embodiments, the MS analysis uses a combination of time-of-flight mass spectrometry (TOF-MS) and electron spray ionization mass spectrometry (ESI-MS). ESI methods are preferred because ions are generated directly in solution and therefore, ESI can be readily combined with other spectral analysis methods, such as HPLC. Although not limiting to the present description, the charge mode of ESI can be varied according to the sample being analyzed. For example, samples derived from plants and cellular extracts are typically analyzed in the positive ion ESI mode. On the other hand, samples containing mostly organic acids (such as a urine sample, for example) are typically analyzed in the negative ESI mode.

In mass spectrometry, each separated component of the sample yields multiple spectral peaks with a measured mass-to-charge (m/z) ratio. Variations in mass measurement can be reduced by normalization against an internal reference standard. In an aspect, spectral peaks can be grouped, into 3-D peaks, according to m/z ratio and retention time. In an aspect, the magnitude parameter, m/z ratio and retention time for each peak are stored in a text-readable format. In another aspect, the magnitude parameter, m/z ratio and retention time are stored in a text-translatable format. In yet another aspect, the magnitude, m/z ratio and retention time are stored in text format and displayed as a graphical representation.

In the methods described herein, the 3-D peaks obtained by MS analysis of a sample are associated or grouped on the basis of particular chemical or molecular features. In an aspect, 3-D peaks are associated or grouped into isotope clusters. In another aspect, isotope clusters are associated into molecular features characterized by their neutral masses and retention times. In yet another aspect, 3-D peaks are grouped into adducts, dimers, and charge states. In an aspect, non-chromatographic background is removed by subtracting the baseline. In another embodiment, molecular features obtained from MS analysis of a sample are normalized before comparison with molecular features obtained from MS analysis of a known compound.

The present disclosure describes a method for differential analysis of components in different samples or groups of samples. In some embodiments, the differential analysis compares expression levels of the components in a first sample with expression levels of the components in a second sample. In another embodiment, parameters for a chemical component in a sample can be compared with parameters for a known component. In an aspect, the associated or grouped spectral peaks for separated components in a sample are compared with the associated or grouped spectral peaks obtained from MS analysis of a known material. In an aspect, the known material is a peptide. In another aspect, the known material is a nucleic acid.

In some embodiments, the methods for MS analysis of biological samples include extracting molecular features from the spectral data. In some embodiments, the analysis comprises identifying molecular features from a sample at a given retention time value, and then associating the identified molecular feature with the molecular features of a known material. In an aspect, associating molecular features comprises identifying and grouping isotope clusters. In another aspect, associating molecular features comprises identifying and grouping neutral mass components in the sample. In some embodiments, the extraction of molecular features from the spectral data comprises associating spectral peaks into 3-D peak, 3-D peaks into isotope clusters, and isotope clusters into molecular features on the basis of ion charge at a given retention time.

Methods for the differential profiling of biological samples, comprising compiling extracted molecular features from a plurality of responses or data sets are described herein. The compiled features from the plurality of responses are stored in a text-readable format, or in a text-translatable format. In an aspect, compiled molecular features for a first sample are cross-aligned with compiled features for a second sample. Statistical methods are then used to normalize the cross-aligned molecular features. In an aspect, differential analysis is performed using standard statistical methods. Differentially expressed features can also be identified visually, through graphical representation. In an aspect, a graphical representation is a plot of Log ratio versus retention time. In another aspect, a graphical representation is a Log/Log ratio plot.

The methods described herein can also be utilized to isolate compounds of interest. For example, after markers (compounds that change in abundancy between or among samples) are identified by differential profiling, their properties (retention time, mass, etc.) can be used as criteria for isolation and purification from samples. The markers can then be studied in further detail.

Systems for Differential Analysis of Samples

A system for differential analysis of samples is described herein. In some embodiments, the system comprises a first apparatus for separating a complex biological sample into chemical components on the basis of retention time and a second apparatus that determines the mass of each of the separated chemical components. The retention time data and mass data for each separated component are retained in a storage medium. The system includes a processing subsystem that associates or groups the separated components on the basis of properties including retention time and mass. The system also includes an output subsystem for displaying the association of the separated chemical components. In some embodiments, the first apparatus comprises a liquid chromatography column, a gas chromatography column, or a capillary electrophoresis device.

In some embodiments, the processing subsystem associates the components on the basis of spectral peak intensity. In another embodiment, the processing subsystem determines a magnitude parameter for each 3-D peak based on the intensity of the spectral peak, the retention time and measured m/z. In an aspect, the magnitude parameter is the volume of the 3-D peak. The processing subsystem associates 3-D peaks according to chemical properties, such as mass or charge state. In another aspect, the subsystem associates 3-D peaks into isotope clusters. In one embodiment, the processing subsystem can be used as part of a differential analysis system. The processing subsystem may optionally compare the associated spectral peaks for the components of the sample with the associated spectral peaks for a known material, to identify one or more components in the sample.

The system includes a storage medium for retaining the retention time and mass for each separated chemical component in a sample. In some embodiments, the storage medium is a computer-readable medium that stores a plurality of data objects. The stored data objects include data objects identifying the retention time for components in the sample, the m/z ratio for components in the sample, and other chemically relevant attributes of components within the sample. Chemically relevant attributes include charge states, isotope properties and adducts. In another aspect, the stored data objects contain information about peak magnitude or peak volume. The data objects to be stored on the computer-readable medium may be further selected on the basis of signal strength. In an aspect, only data objects having signal strength greater than a prescribed value are stored on the computer-readable medium. The data objects stored on the computer-readable medium can be manipulated as text. In some embodiments, data objects are stored in data base form, such that data objects identifying retention time, m/z ratio and peak magnitude are displayed as related objects in a record.

Some embodiments of this invention provide a computer-readable medium comprising executable instructions for performing the analysis methods described herein. For example, the method to be performed can be a method for dividing the mass spectral data from a sample into feature groups, each feature group relating to a compound, wherein said dividing is performed based on retention time, mass to charge ratio, and optionally at least one property selected from the group consisting of isotope clustering, mass, adduct formation, dimer formation, and trimer formation. The method may further comprise allowing the user to filter in or out compounds of interest based on one or more properties selected from the group consisting of retention time, mass, isotope pattern, charge state, abundance, mass defect, and number of ions, for example. The method may be a differential profiling method, in which each sample in a collection of multiple samples is first analyzed as described above, then the results from the multiple samples are compared to each other or one another to identify the differences.

EXAMPLES

In this disclosure, the following abbreviations have the following meanings unless indicated otherwise. Abbreviations not defined have their generally accepted meanings.

| | |
|---|---|
| °C. = | degree Celsius |
| hr = | hour |
| min = | minute |
| sec = | second |
| mM = | millimolar |
| μM = | micromolar |
| nM = | nanomolar |
| ml = | milliliter |
| μl = | microliter |
| nl = | nanoliter |
| mg = | milligram |
| μg = | microgram |
| HPLC = | high performance liquid chromatography |
| LC = | liquid chromatography |
| MS = | mass spectrometry |
| MFE = | Molecular Feature Extractor |
| ppm = | parts per million |

Example 1

Molecular Feature Extraction of Complex LC/MS Data

This example describes a software for complexity reduction of liquid chromatography/mass spectrometry (LC/MS) data. This program, the Molecular Feature Extractor (MFE), combines coeluting spectral peaks into compounds, accurately calculating their neutral mass and abundance while removing chemical interferences. MFE is equally effective in small molecule (such as metabolites) and large molecule (such as peptides) applications. Complex peptide mixtures with known amounts of spiked proteins were first analyzed using MFE, and Genespring MS (Agilent Technologies, Santa Clara, Calif.) software was used to show that the known proteins were not only found but accurately quantified.

Biomarkers are metabolites, peptides, and other biomolecules that can be used to determine the presence or absence of a specific condition such as a disease. LC/MS-based platforms are rapidly becoming popular for the discovery of new biomarkers. The general strategy for doing this is to isolate the type of biomarker from a biological sample (e.g. blood) and then perform reversed phase LC/MS on the resulting mixture. The major challenge for such analyses is the complexity of the sample, which can have concentrations spanning up to 12 orders of magnitude and can contain hundreds of thousands of components. Further, LC/MS systems separate the signal for a single component in the mixture into 100's of different peaks in the mass spectral data, and reconstructing the molecular entities is a rather difficult task. Furthermore, the high throughput and resolution of mass spectrometers result in data files that can be up to several gigabytes in size. Thus, accurate and high throughput data reduction is one of the critical steps in such a biomarker analysis platform.

Here, we demonstrate the utility of MFE using a complex peptide mixture.

Method

Figure 2:
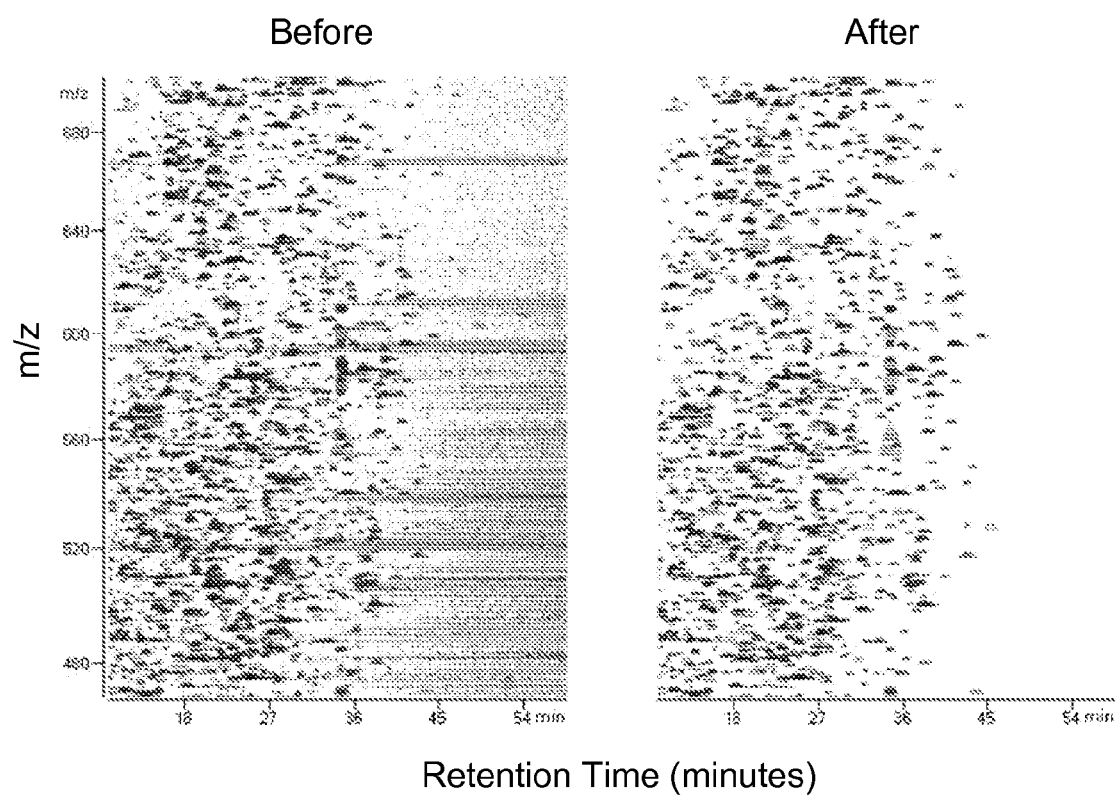
FIG. 2 shows the effect of noise reduction in an MS spectrum. The pattern before noise reduction is on the left, while that after noise reduction is on the right.

MFE (Molecular Feature Extractor) takes raw MS data as the input and outputs a list of "molecular features." A molecular feature represents a chemical entity in the real world, such as a compound (e.g., a peptide). MFE identifies a feature by its mass and retention time (RT or elution time), together with the information on all its isotope clusters, associated with different ion species such as different charge state, dimers, and adducts. The algorithm procedure can be summarized as follows:

Removal of background chemical noise. Background noise is generally concentrated at certain m/z values and distributed evenly throughout the LC/MS run. FIG. 2 shows contour plots of the signals from a peptide mixture before and after the removal of chemical noise. For example, the program can remove all signals with a signal/noise ratio of less than 2.

Extraction of three dimensional peaks (m/z, RT, and peak height are the three dimensions). Each peak is a single isotopomer of a molecular feature.

Grouping of 3-D peaks into isotope clusters. Peaks that belong to the same isotope cluster elute from the chromatographic column at the same time and are spaced at regular intervals that reflects the charge state of the isotopic cluster. However, this may not be sufficient since overlapping, coeluting isotopic clusters are common. Thus, the heights of the peaks in the same isotopic cluster can be taken into account based on knowledge of chemical composition of the compounds in the sample. For example, the ratio between the amounts of naturally occurring $^{12}C$ and $^{13}C$ is known. If two coeluting peaks A and B differ in mass by 1, and the ratio between the heights of A and B equals (within tolerable error) the ratio of $^{12}C/^{13}C$ abundancy, then A and B correspond to the same compound except that they contain $^{12}C$ and $^{13}C$, respectively.

Grouping isotope clusters into molecular features. The separate isotopic clusters for a given molecular feature elute at approximately the same time. These sets of isotope clusters with the same RT are grouped into different molecular features by their associated mass and according to chemistry rules such as the presence of salt adducts.

Figure 3:
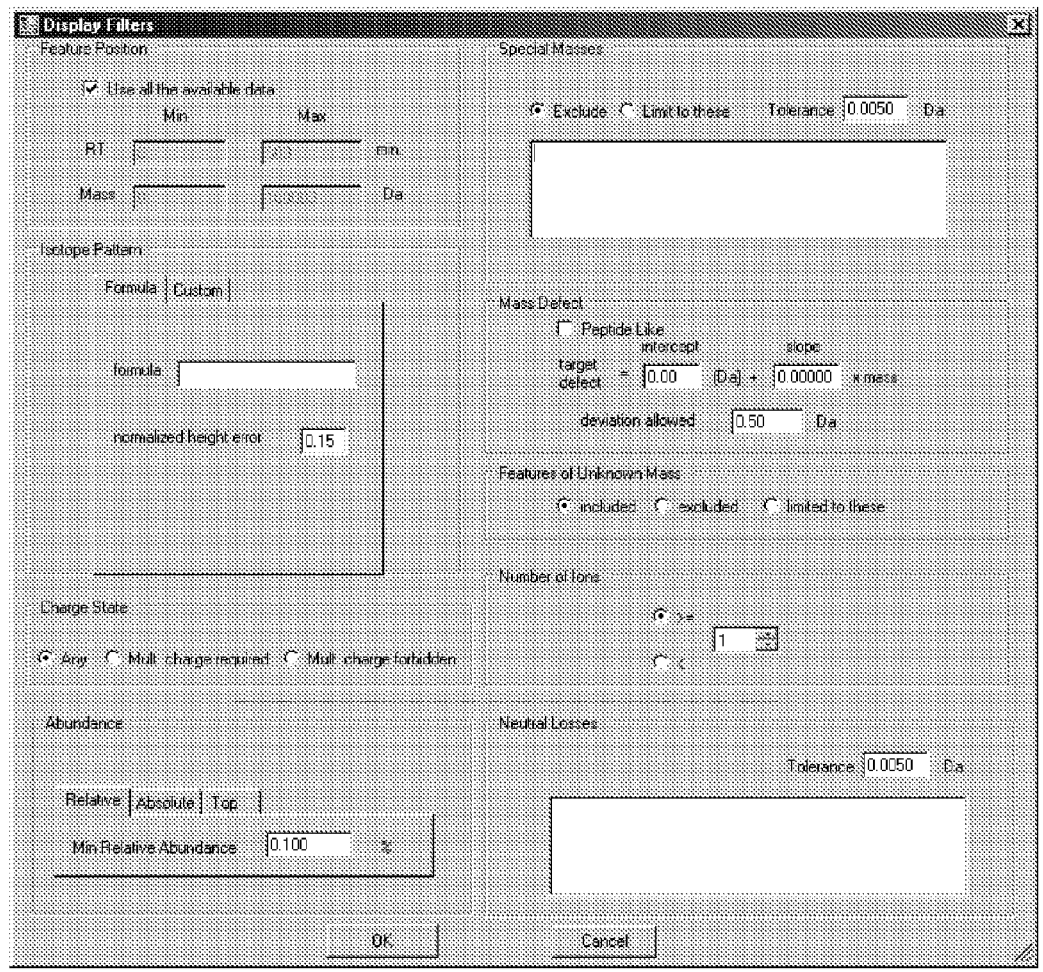
FIG. 3 shows a graphic user interface for filtering the data according to the user's choice.

The user is provided with the option of many filters, which can be used individually or in combination, to separate the result into different categories based on their chemical properties and relationship, and/or the goal of the user. For example, FIG. 3 shows a graphical user interface that lists many filters. Thus, the user can choose a specific range of retention time and/or mass to include in the analysis. Similarly, the user can choose the isotope pattern, charge state, abundance, etc. of the spectral peaks that the user wishes to include in the analysis.

Results and Discussion

To measure the speed performance of MFE, we used a data set acquired during 70-minute LC-MS run that has 238,163,145 data points. MFE extracted 2043 molecular features from this dataset within 5 minutes. Since the data was originally acquired over 70 minutes, this analysis time is fast enough for a high throughput system.

A key feature of a biomarker discovery platform is the ability to detect small but significant changes in concentrations for proteins between a normal and a diseased sample within a highly complex mixture. To test this, a digest of the complete set of cytosolic proteins from *E. coli* was split three ways, with 100, 200, and 400 fmol of a tryptic digest of bovine serum albumin (BSA) and 200, 100, and 50 fmol of a tryptic digest of serotransferrin added to these three samples, respectively. Each sample was run five times using LC/MS and each of the 15 resulting datafiles (~300 MB each) was analyzed using MFE to create lists of components. The resulting compounds were loaded into GeneSpring MS, filtered by fold change and the requirement that a compound must be present in 4 out of 5 datafiles for each condition, and subjected to K-means clustering. The resulting sets were submitted to Agilent Spectrum Mill Proteomics Workbench for manual peptide mass fingerprinting (PMF), and BSA and serotransferrin were successfully identified. It had been expected that the signals for BSA and serotransferrin should change in magnitude proportional to the amount of the corresponding protein in the sample. Indeed, the BSA peptides increased in intensity across the three samples while the serotransferrin peptides decreased in intensity, as expected.

Example 2

Differential Detection of Metabolites

Metabolic samples typically are highly complex, containing hundreds to thousands of compounds, many of which co-elute, spanning a broad range of concentration and compound classes. These characteristics result in significant data-processing challenges. In this work we illustrate the use of two new MS informatics tools designed to facilitate rapid differential analysis of samples for metabolic profiling applications. The MFE algorithm extracts chemically qualified molecular features from complex LC-TOF data sets. Mass Profiler software combines capabilities for cross-sample alignment of molecular features in both the retention time and mass dimensions, including several normalization options, with statistical methods and visualization tools to aid in identification of differentially expressed features. The software tools are applied to differential profiling of metabolites present in rat urine, Arabidopsis plant extracts, and pancreatic islet cell extracts, and accurate mass data are used in determining the chemical compositions and identities of differentially expressed features.

Method

Accurate mass LC-ESI-MS data obtained from urine, cell and plant extracts were used to evaluate the performance of the MFE algorithm and Mass Profiler software. Mass spectral data were acquired with an Agilent LC/MSD TOF. Sample introduction and chromatographic separations were performed with an Agilent 1100 series capillary HPLC system. Minimal sample preparation (desalting, enrichment) was completed prior to analysis using commercially available desalting spin tubes and micropipette tips.

Experimental

Instrumentation:

Agilent 1100 Series Capillary HPLC system interfaced to an Agilent LC/MSD TOF mass spectrometer via a standard or a capillary-optimized ESI source.

Sample Preparation:

Rat urine samples contained 5 mM sodium azide as a preservative to insure the stability of the samples. Minimal sample preparation included 100-fold dilution with HPLC grade water and filtration prior to analysis. The plant extract sample was dissolved in 320 µL acetonitrile, 16 µL of the supernatant was mixed with 4 µL of water and 1 µL was injected. Desalting using C18 coated pipette tips was used for a portion of the plant and cellular extracts.

Chromatographic Conditions:

Chromatographic separation of the organic acids present in the rat urine was accomplished using a C18 3.5, 2.1×100 mm column, with a flow rate of 400 µL/min, solvent gradient: 0-6 min, 0%-20% B; 6-10 min, 20%-95% B; 10-11 min, 95-100% B; with a 3 minute hold time and injection volume of 3.0 µL. Chromatographic separation of the metabolites present in the plant extract was performed on a Zorbax SB C18, 5.0, 150× 0.5 mm column, flow rate of 20 µL/min, solvent gradient: 0-5 min, 5% B, 5-25 min, 5%-95% B with a 20 minute hold and an injection volume of 1.0 µL. The mobile phase solvents were changed from 0.1% formic acid (Water A, Acetonitrile B); to 0.1% acetic acid to reduce the formation of sodium bound dimers from the presence of sodium in the rat urine samples.

Mass Spectrometer Conditions:

Electrospray data for the rat urine samples was obtained using orthogonal ESI optimized with flow rate: at 400 µL/min, drying gas temperature: 350° C.; drying gas flow: 9.5 L/min; nebulizer pressure: 40 psig; capillary voltage: 3000 V and fragmenter voltage: 175 V; The plant extracts were analyzed at 20 µL/min using a micro-spray nebulizer with drying gas temperature: 300° C., drying gas flow: 4.0 L/min, nebulizer pressure 20 psig, capillary voltage: 3500 V and fragmenter voltage 215 V. Negative ion ESI mode provided enhanced detection of the organic acids present in the urine samples, while positive ion ESI mode provided enhanced detection of the metabolites in the plant and cellular extracts. For the plant and urine samples the mass spectrometer was operated with a mass range of m/z 50 to 1,100, and 1.29 cycles/second and m/z 100 to 3200 for the cellular extracts To ensure low-ppm mass accuracy, the internal reference mass correction was utilized to correct for scan to scan variations.

Results and Discussion

MFE Algorithm

The MFE algorithm identifies features in MS data by first finding the mass peaks in all mass spectra, and then removing non-chromatographic chemical background. Next, peaks are clustered in RT (in seconds) and m/z to form 3-D peaks. The 3-D peaks are centroided and a peak volume determined for each peak. Related 3-D peaks (isotopes, adducts, dimers, trimers, multiple charge states) are combined and assigned a neutral mass and total volume.

Figure 4:
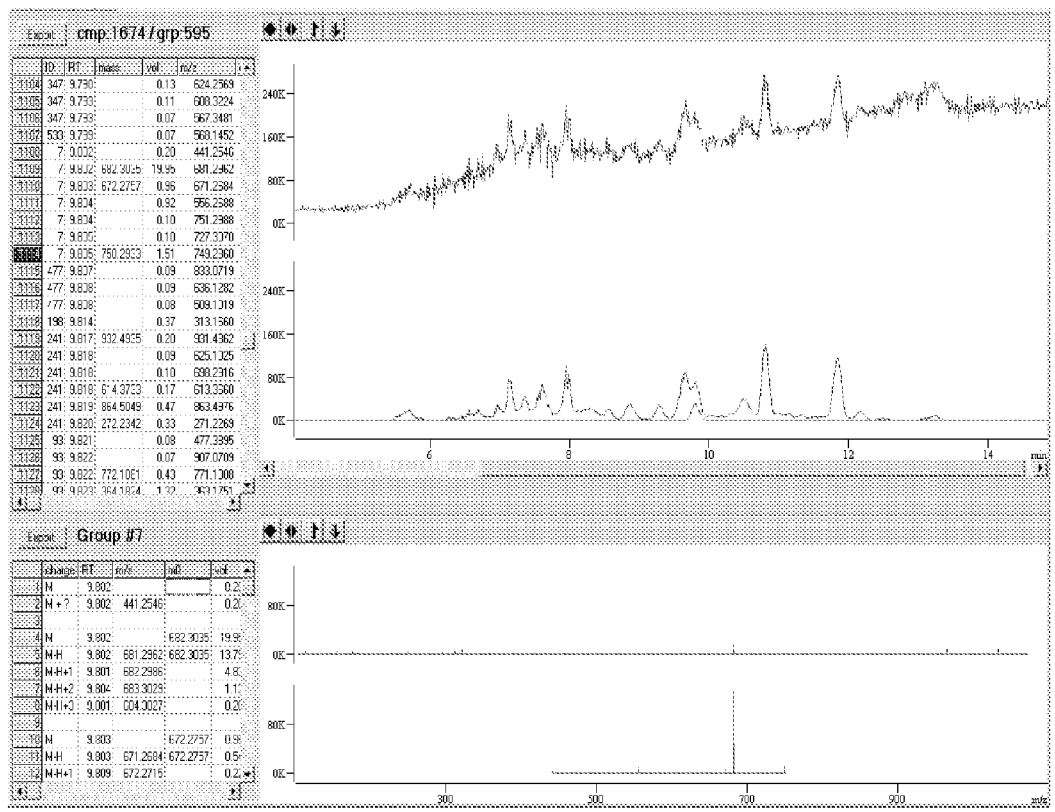
FIG. 4 is a screen capture showing background-subtracted mass spectra and TIC from salt containing cellular extract.

An example of the output is shown below in FIG. 4, including raw, background-subtracted, and extracted feature chromatograms, the list of detected grouped features including RT, m/z and volume values, and an example of an extracted mass spectrum for one of the features.

Dynamic Range Evaluation

Since the MFE algorithm generates feature lists for input to differential expression analysis, we have evaluated its performance over an extended dynamic range. A representative rat urine sample was extracted using a signal-to-noise threshold of 2 and the resulting molecular feature list sorted by peak volume. The largest peak volume (m/z 178.052) was found to be 200 arbitrary units. By inspection, several molecular features were identified at m/z 160.040 with various retention times, and with relative volumes between 0.04% and 1%. The results were compared to the features identified via manual extraction of the m/z 160.040 ion from the raw data set using Analyst QS data analysis software (Sciex, Toronto, Canada). For every molecular feature studied, there was a corresponding peak in the extracted ion chromatograph, exhibiting good agreement for both retention time and relative abundance, over greater than 3 orders of magnitude.

Mass Profiler

In biomarker discovery, carefully designed protocols for sample collection, handling, preparation and analysis must be followed to enable meaningful differential analysis. Appropriate statistical analysis then allows segregation of experimental and within-population variations from cross-population expression level changes. The Profiler software compensates for scan-to-scan shifts in retention time (seconds) and measured masses (ppm). Common features are identified and cross-sample response relative standard deviation values are calculated. Results filters can be used to reduce the number of differentially expressed metabolites to be investigated.

Figure 5:
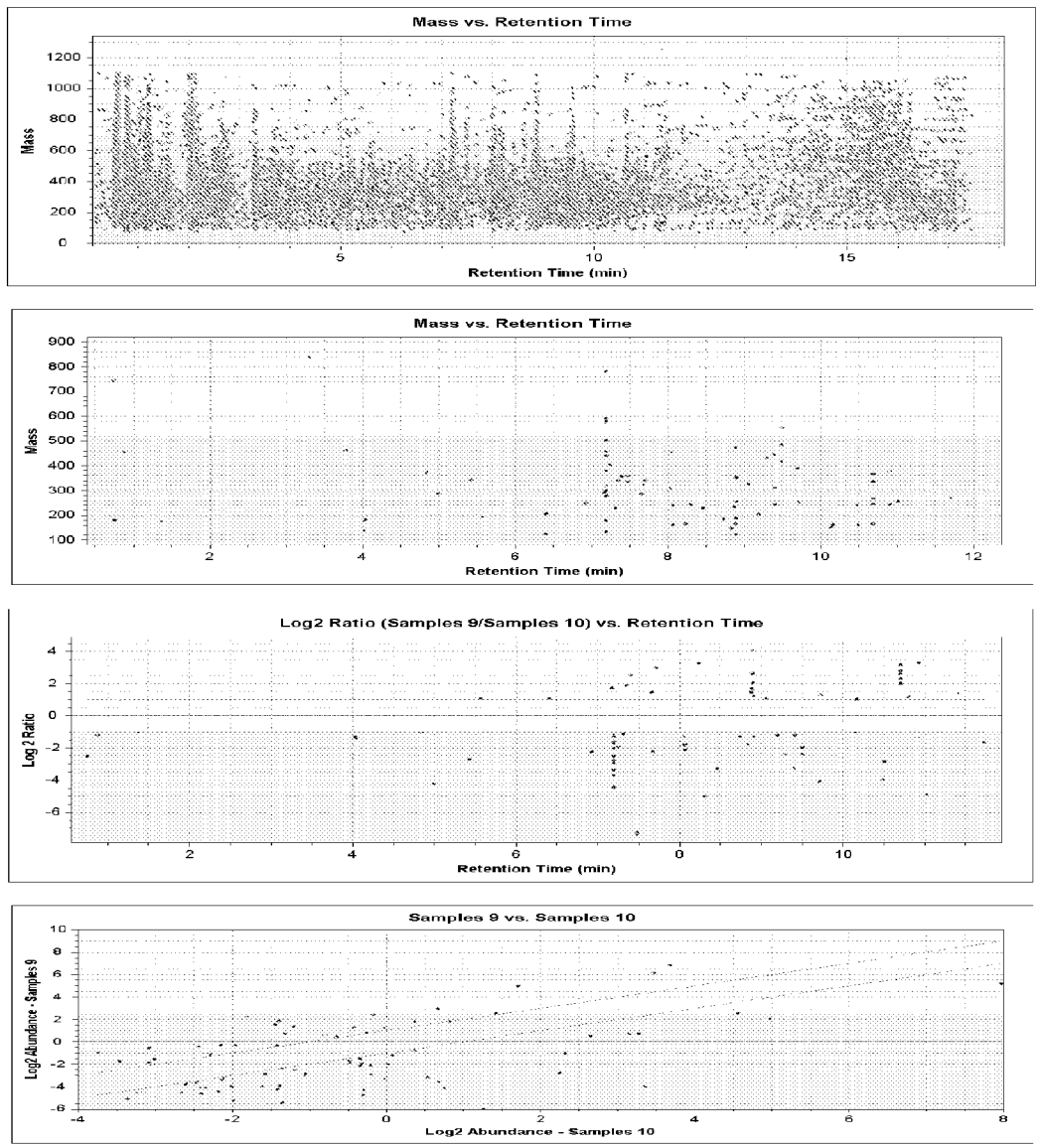
FIG. 5 shows total number of features as a function of m/z and retention time. From the top: (a) no filtering and (b) features present in all samples and at least 2× variation in relative response, (c) Log ratio versus retention time, and (d) Log/Log plot.

Over 13,192 total features were extracted from the two sets of 3 replicates each of rat urine LC/MS data (FIG. 5a). However, only 699 features were present in all six LCMS data sets and only 84 features exhibited a response difference of a factor of 2 or greater across the two sample sets (FIG. 5b). Differential expression changes are readily visualized using the Log ratio versus retention time and Log/Log ratio plots (FIGS. 5c and 5d).

Chemical Identification of Metabolites

Figure 6:
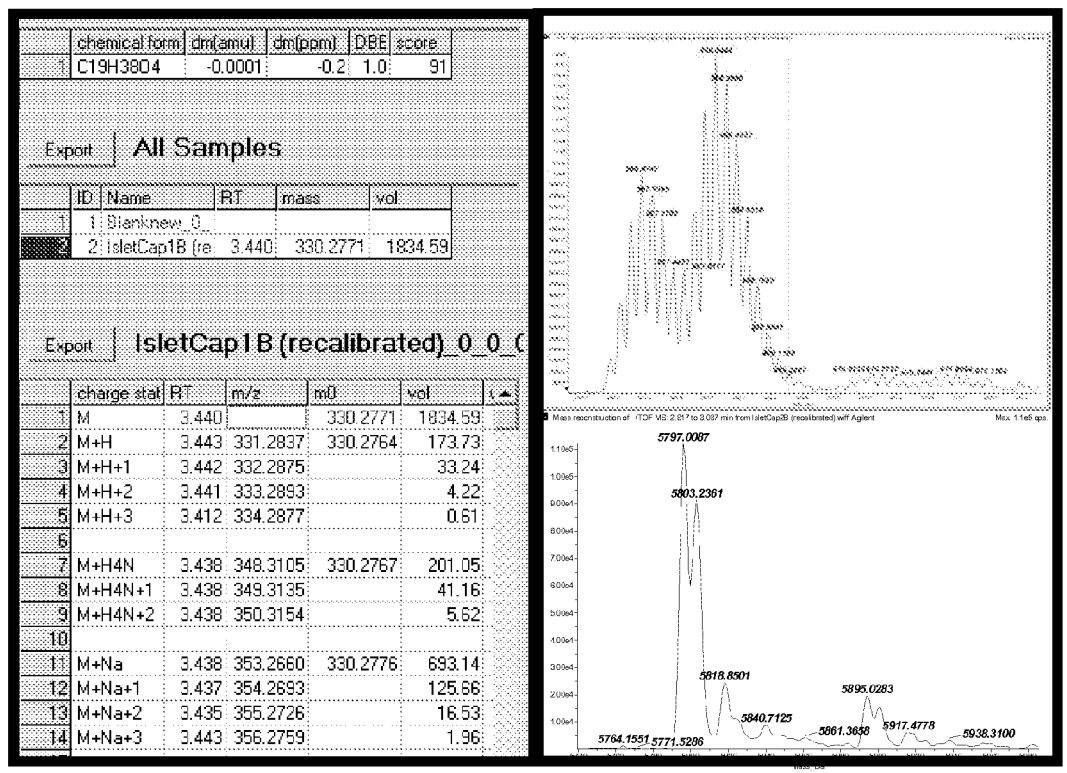
FIG. 6: (a) (left panel) graphical output of chemical identification in profiler; (b) (upper right panel) zoom of multiple charge components of insulin; and (c) (lower right panel) deconvoluted mass spectrum.

Following differential expression analysis, a next step is frequently the chemical identification of differentially expressed features. Chemical identification capabilities are demonstrated using LCMS TOF data obtained from a pancreatic islet cellular extract. The sample is a complex mixture of low molecular weight metabolites (amino acids, glycerolesters, fatty acids) and insulin. The Profiler software employs the measured mass to determine putative elemental compositions. For example, the feature at 3.440 minutes corresponds to glycerol monopalmitate with an empirical formula of $C19H3804$, a mass error of −0.2 ppm and an isotope match of 91 (FIG. 6a). Deconvolution of multiple charge states by the software confirmed residual insulin (FIGS. 6b/6c).

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention.

The invention claimed is:

1. A method of analyzing mass spectral data obtained from a sample, comprising:
   dividing the mass spectral data into feature groups, wherein each of said feature groups relates to a compound; and
   filtering the data based on properties selected from the group consisting of retention time, mass, isotope pattern, charge state, abundance, mass defect, and number of ions.

2. The method of claim 1, wherein said dividing is performed based on retention time, mass to charge ratio, isotope clustering, adduct formation, dimer formation, and trimer formation of spectral peaks.

3. The method of claim 1 further comprising comparing the properties of at least one feature group to the properties of a known material to identify one or more components in the sample.

4. The method of claim 1, wherein the sample is a biological sample.

5. A method for differential profiling multiple sets of mass spectral data, wherein each set of the mass spectral data is obtained from a distinct sample, the method comprising:
   (a) analyzing each set of mass spectral data according to the method of claim 1;
   (b) comparing the results of step (a) from different samples to identify compounds that are present in different amounts between or among the samples.

6. A computer-readable medium comprising executable instructions to perform the method of claim 1.

7. A system comprising the computer-readable medium of claim 6.

8. The system of claim 7 further comprising a mass spectrometer.

9. The system of claim 8 further comprising at least one liquid chromatography column.

10. The system of claim 8 further comprising at least one gas chromatography column.

11. The system of claim 8 further comprising at least one capillary electrophoresis apparatus.

12. The system of claim 8 wherein the mass spectrometer comprises an ion source selected from the group consisting of electrospray, matrix assisted laser desorption (MALDI), and photoionization ion sources.

13. The system of claim 8 wherein the mass spectrometer comprises a mass analyzer selected from the group consisting of quadrupole, time-of-flight, ion trap, and fourier transform-ion cyclotron resonance (FT-ICR) mass analyzers.

14. A method of comparing the compositions of multiple samples, comprising:
   (a) separating at least part of the components in each sample;
   (b) analyzing the separated components in each sample with a mass spectrometer to generate a mass spectral data set for each sample;
   (c) recording the multiple mass spectral data sets; and
   (d) analyzing each of the mass spectral data sets according to the method of claim 1 and comparing the results from said multiple samples.

15. The method of claim 14, wherein said dividing is performed based on retention time, mass to charge ratio, isotope clustering, adduct formation, dimer formation, and trimer formation of spectral peaks in the mass spectral data.

16. The method of claim 14 further comprising comparing the properties of at least one feature group to the properties of a known material to identify one or more components in each of the samples.

17. The method of claim 14, wherein the multiple samples are biological samples.

18. The method of claim 14, wherein the at least part of the components are separated in step (a) by liquid chromatography.

19. A method for differential profiling multiple sets of mass spectral data, wherein each set of the mass spectral data is obtained from a distinct sample, the method comprising:
   (a) dividing the mass spectral data from each sample into feature groups, each feature group relating to a compound, wherein said dividing is performed based on retention time, mass to charge ratio, and optionally at least one property selected from the group consisting of isotope clustering, mass, adduct formation, dimer formation, and trimer formation; and
   (b) comparing the results of step (a) from different samples to identify compounds that are present in different amounts between or among the samples.

20. A computer-readable medium comprising executable instructions to perform the method of claim 19.

* * * * *